(12) United States Patent
Lee et al.

(10) Patent No.: US 7,242,201 B2
(45) Date of Patent: Jul. 10, 2007

(54) APPARATUS AND METHOD FOR DETECTING STATE OF HEAT EXCHANGER TUBE

(75) Inventors: Deok Hyun Lee, Seoul (KR); Myung Sik Choi, Daejeon (KR); Do Haeng Hur, Daejeon (KR); Jung Ho Han, Daejeon (KR)

(73) Assignees: Korea Atomic Energy Research Institute, Daejeon (KR); Korea Hydro & Nuclear Power Co., Ltd., Seoul (KR)

( * ) Notice: Subject to any disclaimer, the term of this patent is extended or adjusted under 35 U.S.C. 154(b) by 9 days.

(21) Appl. No.: 11/264,597

(22) Filed: Nov. 1, 2005

(65) Prior Publication Data

US 2007/0018661 A1    Jan. 25, 2007

(30) Foreign Application Priority Data

Jul. 20, 2005  (KR) .................... 10-2005-0065899

(51) Int. Cl.
  G01R 27/08  (2006.01)
  G01N 27/82  (2006.01)
  G01N 27/26  (2006.01)

(52) U.S. Cl. .................. 324/718; 324/242; 204/404; 205/776.5

(58) Field of Classification Search ............ 324/700, 324/699, 693, 691, 649, 600, 71.2, 718, 456, 324/216, 217, 237, 238, 240, 242; 204/404; 205/775.5, 776.5, 777, 791; 73/592, 598, 73/600

See application file for complete search history.

(56) References Cited

U.S. PATENT DOCUMENTS

| | | | |
|---|---|---|---|
| 4,856,337 A | | 8/1989 | Metala et al. |
| 5,068,608 A | * | 11/1991 | Clark, Jr. ................ 324/220 |
| 5,532,591 A | * | 7/1996 | Logue ................... 324/242 |
| 5,751,144 A | * | 5/1998 | Weischedel ............. 324/240 |
| 6,501,267 B1 | * | 12/2002 | Kurokawa et al. ....... 324/242 |
| 6,519,535 B1 | * | 2/2003 | Petri et al. ............... 702/42 |
| 6,792,069 B2 | * | 9/2004 | Hirabayashi et al. ...... 378/58 |
| 7,038,446 B1 | * | 5/2006 | Keely .................... 324/240 |
| 2006/0288718 A1 | * | 12/2006 | Bradley et al. ......... 62/228.1 |

FOREIGN PATENT DOCUMENTS

KR    10-2005 0078668    8/2005

* cited by examiner

*Primary Examiner*—Andrew H. Hirshfeld
*Assistant Examiner*—Hoai-An D. Nguyen
(74) *Attorney, Agent, or Firm*—Ladas & Parry LLP (57) ABSTRACT

Provided is an apparatus for concurrently detecting a defect occurring in a heat exchanger tube and a geometric transition of the heat exchanger tube. The apparatus for detecting the state of a heat exchanger tube, including: the first detection unit detecting a defect of the heat exchanger tube; and the second detection unit detecting a geometric transition of the heat exchanger tube, in which the first detection unit and the second detection unit are disposed at the same circumferential position of a cylindrical body separately, installed to have a certain distance in the lengthwise direction of the cylindrical body, and inserted inside the heat exchanger tube. According to the present invention, not only a defect but also the type of geometric transition, which may accelerate the initiation and growth of a defect, is identified and the size of the geometric transition is concurrently measured, thereby improving the reliability in early detection of a defect.

12 Claims, 13 Drawing Sheets

APPARATUS AND METHOD FOR DETECTING STATE OF HEAT EXCHANGER TUBE

CROSS-REFERENCE TO RELATED APPLICATIONS

This application claims the benefit of Korean Patent Application No. 10-2005-65899, filed on Jul. 20, 2005, in the Korean Intellectual Property Office, the disclosure of which is incorporated herein in its entity by reference.

BACKGROUND OF THE INVENTION

1. Field of the Invention

The present invention relates to an apparatus for detecting the state of a heat exchanger tube, and more particularly, to an apparatus for concurrently detecting a defect generated in a heat exchanger tube and a geometric transition of the heat exchanger tube.

2. Description of the Related Art

The general terminology, heat exchanger tube, includes steam generator tubes and condenser tubes of nuclear power plants, boiler tubes in fossil fuel power plants, and the like. There may be a defect in a heat exchanger tube, such as a crack, a wear, a pit, and an intergranular corrosion. In order to detect a defect of a heat exchanger tube, there is an eddy current test as a conventional nondestructive testing method.

Current conventional eddy current tests include using a probe equipped with a non-surface riding coil and using a probe equipped with a surface riding coil.

Conventional non-surface riding coil probes include a bobbin coil probe and a multi-array coil probe in which a coil is separated from the inner surface of a heat exchanger tube. However, in case of a conventional non-surface riding coil probe, a geometric transition of the inner/outer surface of a heat exchanger tube generates an eddy current signal caused by a gap change between the inner surface of the heat exchanger tube and the coil. In this case, if a defect exists in a shape-changed position, since an eddy current signal caused by a defect is not distinguished from an eddy current signal caused by a geometric transition, a technical weak point of this method is the difficulty in detecting a defect.

To solve the problem, a rotating pancake coil probe is developed, which is a surface riding type probe equipped with springs below a coil such that the coil is in constant contact with the inner surface of a heat exchanger tube. The rotating pancake coil probe rotates the probe by using a motor while moving up and down the heat exchanger tube in a straight line to test a heat exchanger tube. However, in the conventional rotating pancake coil probe, since a coil is in constant contact with the inner surface, in the case a geometric transition exists on the inner/outer surfaces of the heat exchanger tube, an eddy current signal caused by a gap may be minimized, thereby measuring only the eddy current signal caused by a defect, regardless of the geometric transition.

As describe above, due to the characteristics of each conventional probe, in a eddy current test of a commercial power plant, a procedure of accurately detecting a defect by using a surface riding type rotating pancake coil probe on a region of a heat exchanger tube, in which an abnormal signal is generated, after performing a test by using a non-surface riding type probe such as bobbin coil probe is applied. Accordingly, it is impossible to concurrently detect a defect developed in the heat exchanger tube and a geometric transition around the defect, and also to distinguish the defect from the geometric transition by using the conventional testing method.

On the other hand, there may be many types of geometric transitions on the inner/outer surfaces of a heat exchanger tube, such as an expansion, an expansion transition, a bend, a dent in which a local zone is intruded in the direction of the inside diameter, and a bulge in which a local zone is protruded in the direction of the outside diameter. Korean Patent Application No. 10-2004-0006391 discloses an eddy current probe for measuring only a geometric transition in a heat exchanger tube, and there is a technical restriction of not being able to detect a defect in a shape-changed position.

Since the described geometric transition causes a local residual stress in a heat exchanger tube and acts as a structural factor accelerating the evolution of a defect, in particular a crack type defect, it is required to develop a method of concurrently detecting a geometric transition in addition to a defect and distinguishing the defect from the geometric transition in an eddy current test.

SUMMARY OF THE INVENTION

The present invention provides an apparatus and a method for concurrently detecting a defect existing on the inner/outer surfaces of a heat exchanger tube, checking whether a geometric transition exists, identifying the type of the geometric transition, and taking a three-dimensional measurement of the position and the size.

According to an aspect of the present invention, an apparatus is provided for detecting the state of a heat exchanger tube, including: the first detection unit detecting a defect of the heat exchanger tube; and the second detection unit detecting a geometric transition of the heat exchanger tube, wherein the first detection unit and the second detection unit are disposed at the same circumferential(angular) position of a cylindrical body, installed to have a certain distance in the lengthwise direction of the cylindrical body, and inserted inside the heat exchanger tube.

According to another aspect of the present invention, a method of detecting the state of a heat exchanger tube is provided, including: a step of detecting a defect of the heat exchanger tube, the step performed by the first detection unit; a step of detecting a geometric transition of the heat exchanger tube, the step performed by the second detection unit; and a step of collecting signal data about the detected defect and the detected geometric transition and measuring the position in which the defect occurs and the geometric transition exists, as well as the size of the geometric transition, the step performed by a measurement unit, wherein the first detection unit and the second detection unit are disposed at the same circumferential(angular) position of a cylindrical body, installed to have a certain distance in the lengthwise direction of the cylindrical body, and inserted inside the heat exchanger tube.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
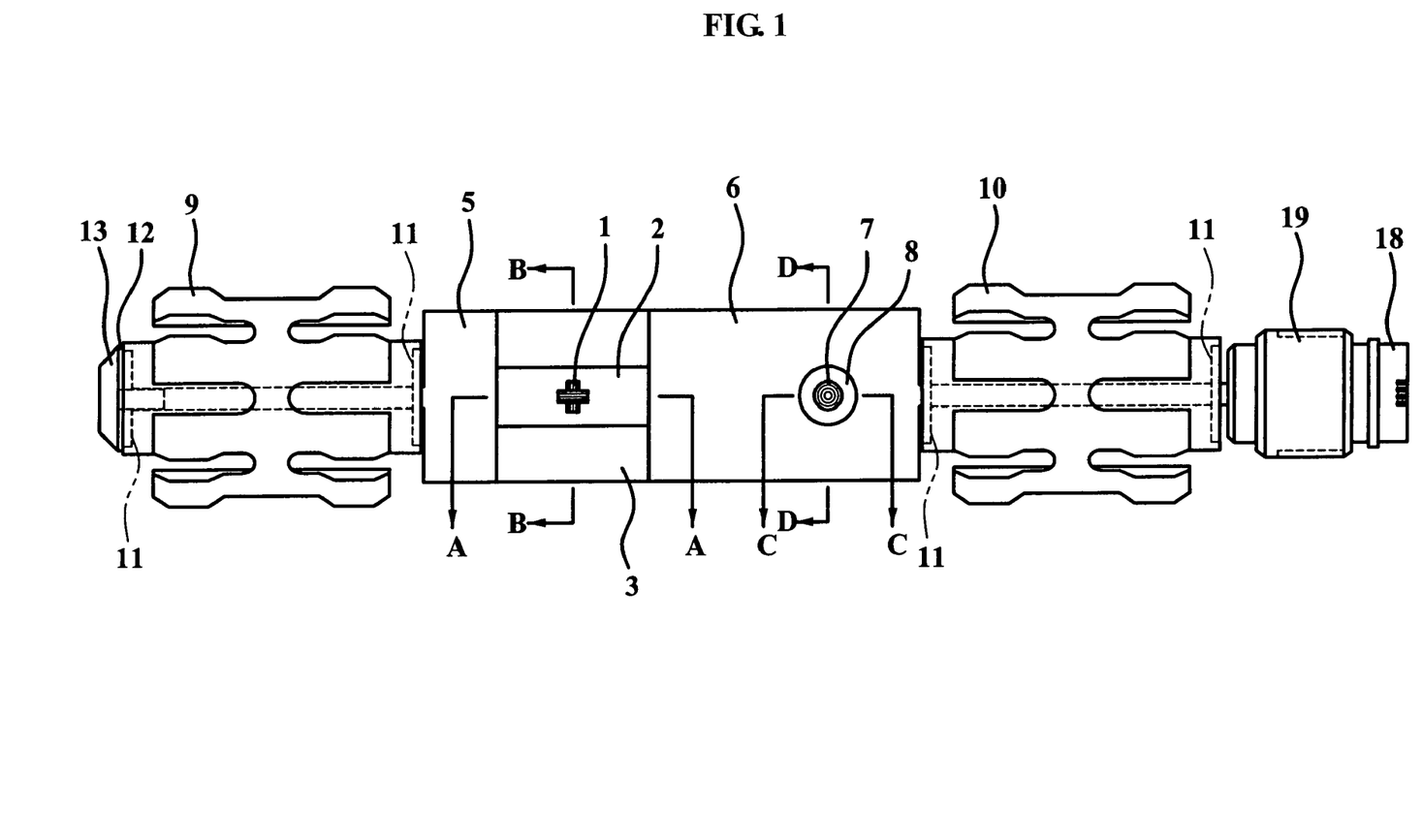
FIG. 1 is a diagram illustrating the structure of a probe detecting the state of a heat exchanger tube, according to an embodiment of the present invention.

FIG. 1 is a diagram illustrating the structure of a probe detecting the state of a heat exchanger tube, according to an embodiment of the present invention.

Referring to FIG. 1, in the probe, a defect detecting eddy current coil 1 is inserted into a surface riding coil support body 2 and a geometric transition detecting eddy current coil 7 is inserted into a non-surface riding coil support body 8.

The defect detecting eddy current coil 1 and the geometric transition detecting eddy current coil 7 are disposed at the same circumferential (angular) location in the cylindrical probe bodies 3, 5, and 6, respectively, installed to have a certain distance in the lengthwise direction of the probe bodies 3, 5, and 6, and the entire probe is inserted into the heat exchanger tube.

The surface riding coil support body 2 and the probe body 3 with a built-in spring are fixed to the probe body 5, which is the upper part, and the probe body 6, which is the lower part, to prevent the surface riding coil support body 2 from being separated from the probe body 3 with the built-in spring.

The cylindrical probe bodies 3, 5, and 6 are supported by an upper support leg 9 and a lower support leg 10, for maintaining balance and stability, which are elastically in contact with the inner surface of the heat exchanger tube such that the outer surface of the body is located concentrically with the inner circle of the heat exchanger tube at a certain distance, so as to not make contact, from the inner surface of the heat exchanger tube in the case the probe bodies 3, 5, and 6 are inserted into the heat exchanger tube. The support legs 9 and 10, elastically in contact with the inner surface of the heat exchanger tube, may be included in the middle part of the cylindrical probe body between the defect detecting eddy current coil 1 and the geometric transition detecting eddy current coil 7.

A bearing 11 is installed at both ends of the support legs 9 and 10 such that the support legs 9 and 10 only move in a straight line without rotation in the case the probe bodies 3, 5, and 6 rotate and move in a straight line inside the heat exchanger tube.

The upper support leg 9 and a front end of the probe are finished with a washer 12 and a bolt 13, thereby preventing the upper support leg 9 from being separated from the probe body 5.

The lower support leg 10 and a terminal of the probe are finished with a conductor socket 18 and a bolt 19 for engagement to the rotating motor axis. Conducting wires 15 and 16 (see FIGS. 2 to 5) for alternating current signal transmission and eddy current signal reception of the defect detecting eddy current coil 1 and the geometric transition detecting eddy current coil 7 are connected to the conductor socket 18 via an inner space 17 (see FIGS. 2 to 5) of the cylindrical probe bodies 3, 5, and 6.

Figure 2:
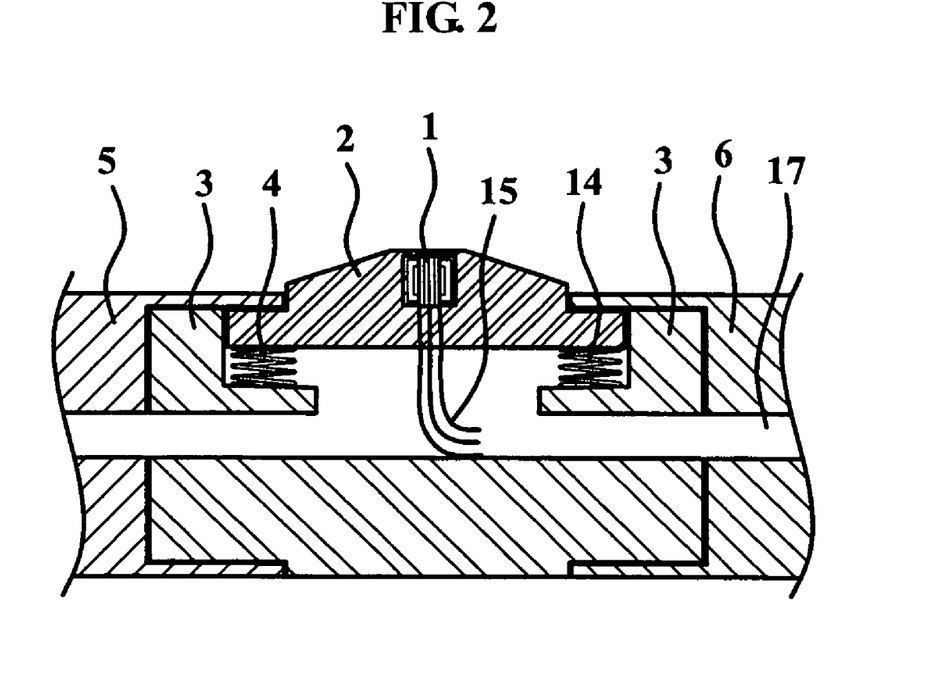
FIG. 2 is a cross-sectional view illustrating A—A in the probe of FIG. 1.
Figure 3:
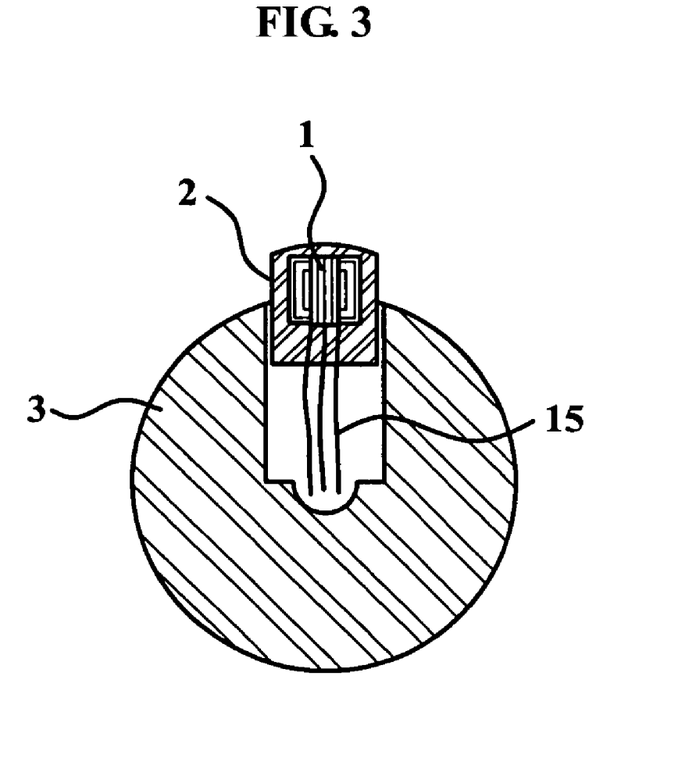
FIG. 3 is a cross-sectional view illustrating B—B in the probe of FIG. 1.

FIGS. 2 and 3 are cross-sectional view illustrating A—A section and B—B section associated with the defect detecting eddy current coil in the probe of FIG. 1, respectively.

Referring to FIGS. 2 and 3, the defect detecting eddy current coil 1 is wound to cross in a horizontal direction and a vertical direction, inserted into the surface riding coil support body 2, and installed in the cylindrical probe body 3 with the built-in spring. The defect detecting eddy current coil 1 is inserted into the heat exchanger tube and rotated by a motor while moving up and down the heat exchanger tube in a straight line to measure an eddy current signal caused by a defect existing in the inner/outer surfaces of the heat exchanger tube, such as a crack, a wear, a pit, and an intergranular corrosion. The probe body 3 with the built-in spring may be equipped with two or more different defect detecting eddy current coils at a certain circumferential (angular) distance on the circumference at the same time. A pair of springs 4 and 14 are installed below both ends of the surface riding coil support body 2 such that the inner surface of the heat exchanger tube, which is the object under examination, is in constant contact with the defect detecting eddy current coil 1. In this case, both ends of the surface riding coil support body 2 are fixed to the cylindrical upper probe body 5 and the cylindrical lower probe body 6 to prevent the surface riding coil support body 2 and the springs 4 and 14 from being separated from the probe body 3. The conducting wire 15 for alternating current signal transmission and eddy current signal reception is connected to the defect detecting eddy current coil 1 via the inner space 17 of the cylindrical probe bodies 3, 5, and 6.

Figure 4:
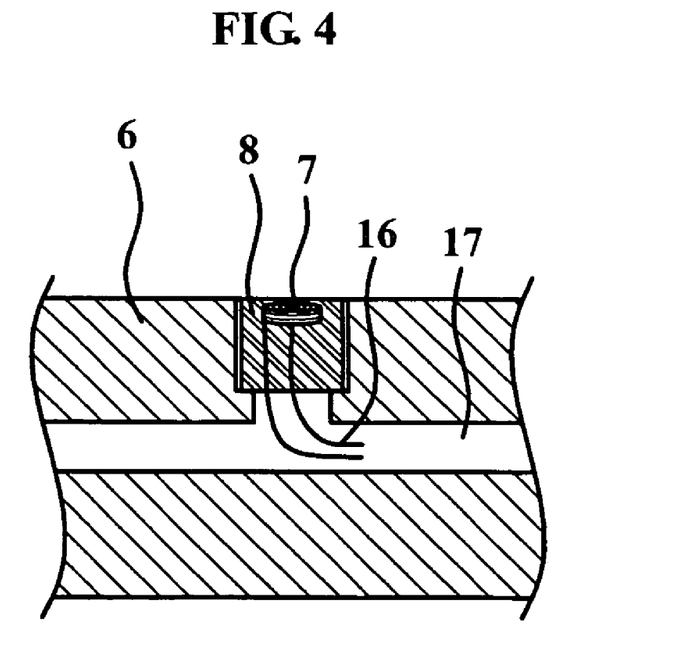
FIG. 4 is a cross-sectional view illustrating C—C in the probe of FIG. 1.
Figure 5:
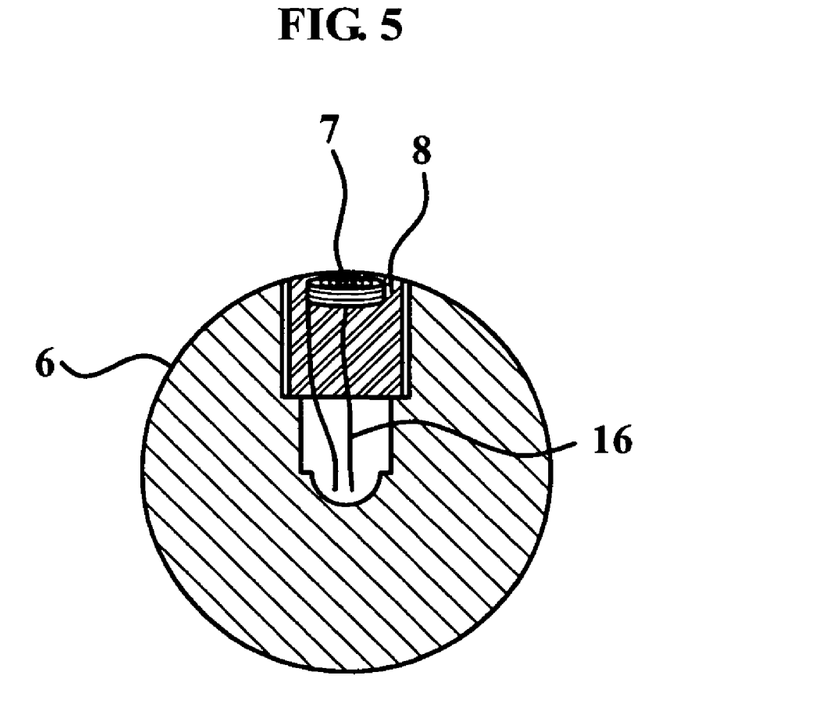
FIG. 5 is a cross-sectional view illustrating D—D in the probe of FIG. 1.

FIGS. 4 and 5 are cross-sectional views illustrating C—C section and D—D section associated with the geometric transition detecting eddy current coil in the probe of FIG. 1, respectively.

Referring to FIGS. 4 and 5, the geometric transition detecting eddy current coil 7 is a coil wound to form a spiral, inserted into the non-surface riding coil support body 8, and fixed to the outer surface of the cylindrical lower probe body 6 to have a certain distance from the inner surface of the heat exchanger tube that is the object under examination. The conducting wire 16 for alternating current signal transmission and eddy current signal reception is connected to the geometric transition detecting eddy current coil 7 via the inner space 17 of the cylindrical probe body 6. The geometric transition detecting eddy current coil 7 is inserted into the heat exchanger tube and rotated by a motor while moving up and down the heat exchanger tube in a straight line to detect an eddy current signal caused by geometric transition such as an expansion, a dent, and a bulge of the heat exchanger tube. The cylindrical lower probe body 6 may be equipped with two or more different geometric transition detecting eddy current coils at a regular circumferential (angular) distance on the same circumference.

FIGS. 6, 7, 8, and 9 illustrate the sequence of a method of concurrently detecting a defect and a geometric transition by using a heat exchanger tube state detecting apparatus according to the present invention, in the first heat exchanger tube sample in which the outer surface of an expansion transition zone is locally dented and a single crack formed from one point extending in a direction along the circumference is located on the inner surface corresponding to the dented outer surface.

Figure 6:
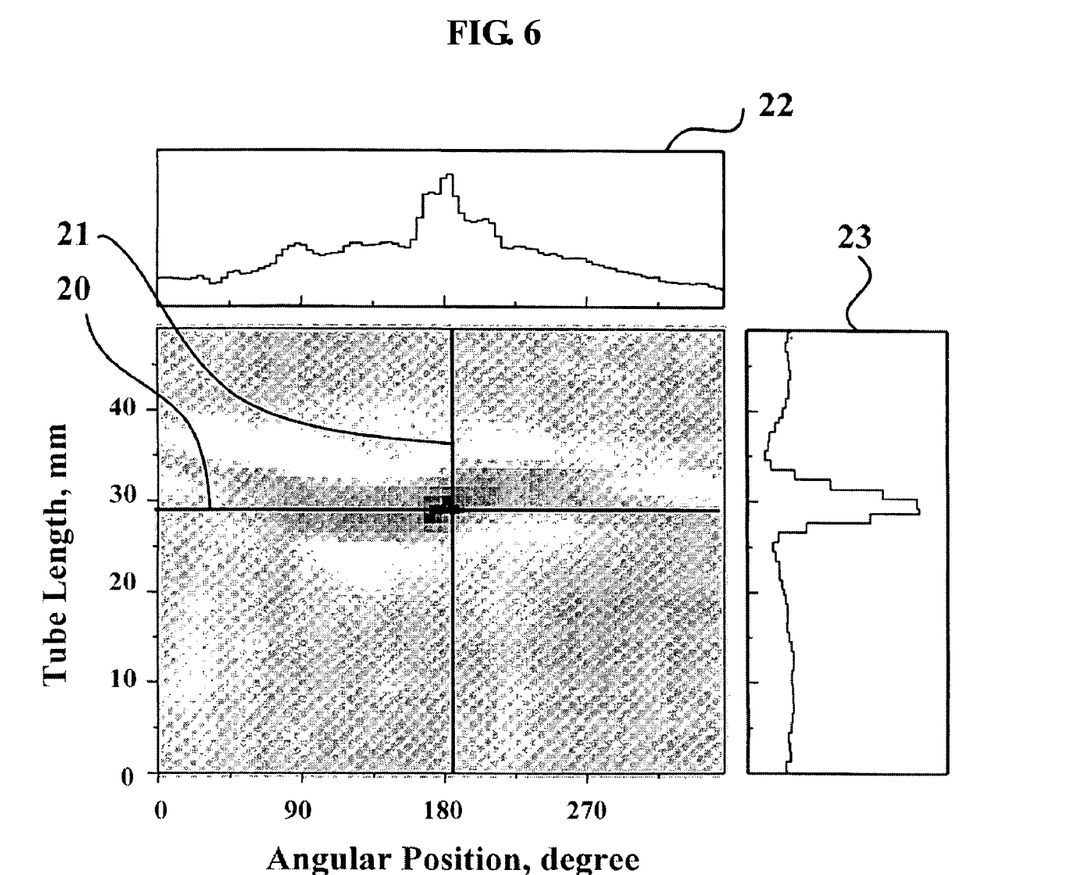
FIG. 6 is a distribution graph of the amplitude of an eddy current signal for each position in the direction of the circumference and length, measured by the coil for detecting a defect in the case a single crack in the direction of the circumference existing in a heat exchanger tube is detected by using a heat exchanger tube state detecting apparatus, according to the present invention.

FIG. 6 is a distribution graph of the amplitude of an eddy current signal for each position in the direction of the circumference and length, measured by the coil for detecting a defect in the case a single crack, formed from one point extending in a direction along the circumference, existing in the first heat exchanger tube sample is detected by using a heat exchanger tube state detecting apparatus, according to the present invention.

Referring to FIG. 6, the horizontal axis indicates positions in the circumferential direction of the heat exchanger tube having a range of 0–360° and the vertical axis indicates positions in the lengthwise direction of the heat exchanger tube. The change of signal amplitudes obtained from each position is indicated as a difference in shading. The first horizon 20 and the first vertical 21 indicate the position of a defect having the largest signal amplitude, which locates the position of the defect as 29 mm in the lengthwise direction and 185° in the circumferential direction, respectively. The first graph 22 indicates the change of signal amplitude for each position in the circumference of a zone disposed on the first horizontal 20, and the second graph 23 indicates the change of signal amplitude for each lengthwise position of a zone disposed on the first vertical 21.

Figure 7:
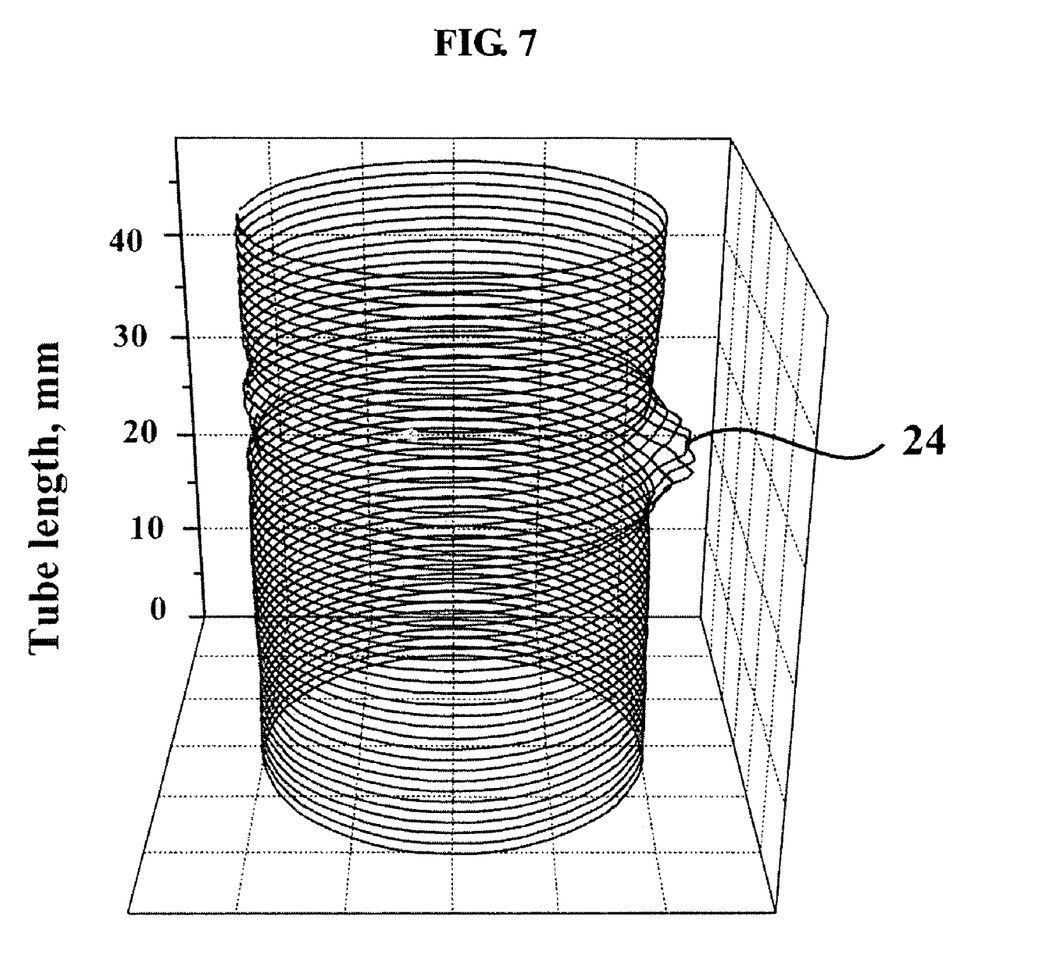
FIG. 7 is a three-dimensional graph of the amplitude distribution of the eddy current signal, measured by the coil for detecting a defect in the case a single crack in the direction of the circumference existing in a heat exchanger tube is detected by using a heat exchanger tube state detecting apparatus, according to the present invention.

FIG. 7 is a three-dimensional graph of the amplitude distribution of the eddy current signal, measured by the coil for detecting a defect in the case a single crack in the direction of the circumference existing in the first heat exchanger tube sample is detected by using a heat exchanger tube state detecting apparatus, according to the present invention.

Referring to FIG. 7, the heat exchanger tube state detecting apparatus may recognize in three dimensions the number of defects to be one and the location 24 of the defect occurring in the exchanger tube by the three-dimensional graph of amplitude distribution of the eddy current signal measured by the defect detecting eddy current coil.

Since the defect detecting eddy current coil and the geometric transition detecting eddy current coil installed in the probe are separated by a certain distance in a lengthwise direction as shown in FIG. 1, a time difference may occur between the collected eddy current signals by the distance of the two coils with respect to the same lengthwise location to be measured in the case of examining the heat exchanger tube. The signals from the two coils may be synchronized to have the information on the same lengthwise location by computing the velocity of the movement of the probe or by measuring the absolute location of the probe in the lengthwise direction. In the case of a position being in the circumferential direction, an additional correction is not required because the two coils are installed in the same circumferential (angular) location.

Figure 8:
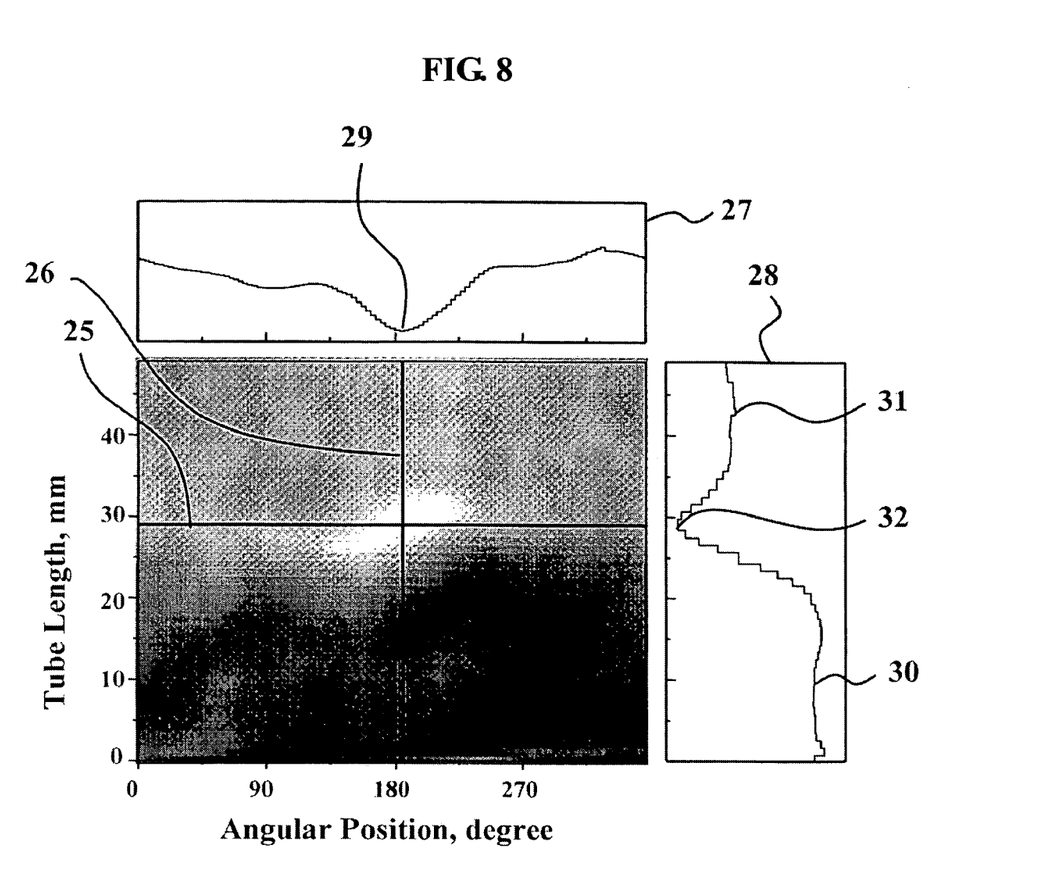
FIG. 8 is a distribution graph of the amplitude of an eddy current signal for each position in the direction of the circumference and length, measured by the coil for detecting a geometric transition in the case a local dent existing in a heat exchanger tube is detected by using a heat exchanger tube state detecting apparatus, according to the present invention.

FIG. 8 is a distribution graph of the amplitude of an eddy current signal for each position in the direction of the circumference and length, measured by the coil for detecting a geometric transition in the case a local dent existing in the first heat exchanger tube sample is detected by using a heat exchanger tube state detecting apparatus, according to the present invention.

Referring to FIG. 8, the heat exchanger tube state detecting apparatus synchronizes the data of eddy current signal amplitude measured from the geometric transition detecting eddy current coil with the data from the defect detecting eddy current coil such that the location of the second horizon 25 and the second vertical 26 are identical with the location of the first horizon 20 and the first vertical 21, respectively. The third graph 27 indicates a signal amplitude change for each circumferential location of a zone disposed on the second horizon 25, and the fourth graph 28 indicates a signal amplitude change for each lengthwise location of a zone disposed on the second vertical 26. Referring to the third graph 27, the location of a defect is a position in which the size of a dent 29 is largest on the circumferential location. Referring to the fourth graph 28, the location of the defect in the lengthwise direction is a dented position 32 within a transition zone between an expanded region 30 and a non-expanded region 31.

Figure 9:
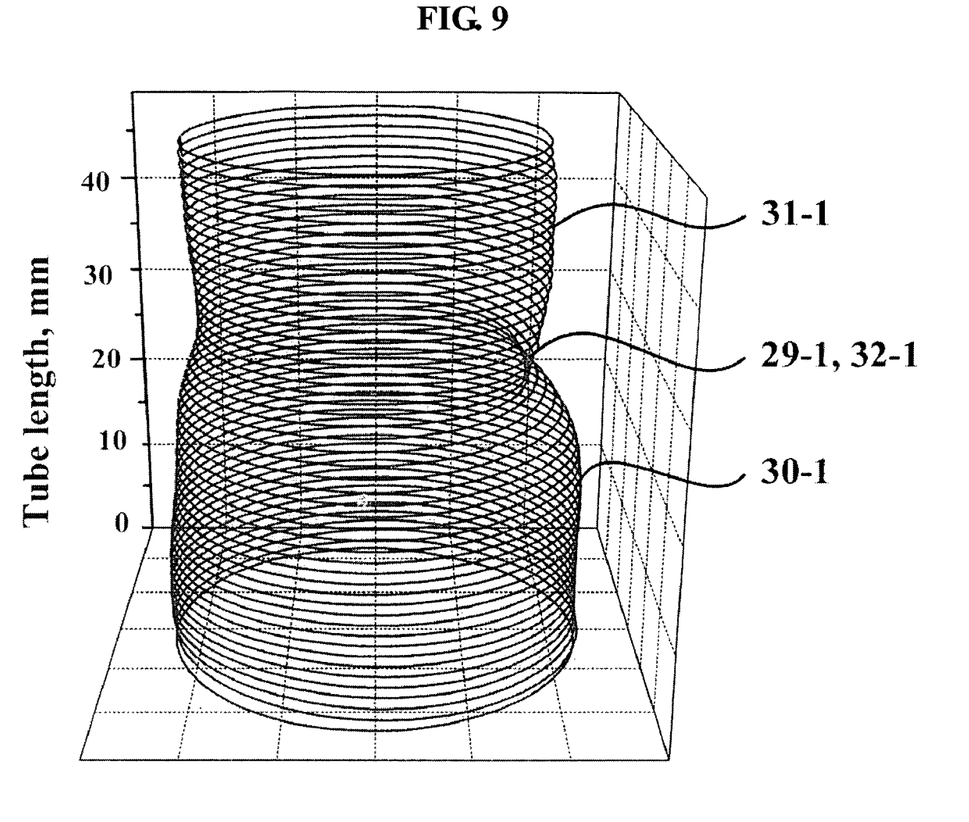
FIG. 9 is a three-dimensional graph of amplitude distribution of the eddy current signal, measured by the coil for detecting a geometric transition in the case a local dent existing in a heat exchanger tube is detected by using a heat exchanger tube state detecting apparatus, according to the present invention.

FIG. 9 is a three-dimensional graph of amplitude distribution of the eddy current signal, measured by the coil for detecting a geometric transition in the case a local dent existing in the first heat exchanger tube sample is detected by using a heat exchanger tube state detecting apparatus, according to the present invention.

Referring to FIG. 9, the heat exchanger tube state detecting apparatus may recognize in three dimensions the change in the diameter of an expanded region 30-1 and a non-expanded region 31-1, and the geometric anomaly that the transition zone between the expanded region 30-1 and the non-expanded region 31-1 is dented 29-1 and 32-1 via the three-dimensional graph of the amplitude distribution of the eddy current signal.

FIGS. 10, 11, 12, and 13 illustrate the sequence of a method of concurrently detecting a defect and a geometric transition by using the heat exchanger tube state detecting apparatus according to the present invention, in the second heat exchanger tube sample in which approximately a 60° range section of the circumference is protruded over the length of approximately 40 mm in the direction of the outside diameter and a crack is formed on the inner surface of the protruded center in the lengthwise direction of the tube.

Figure 10:
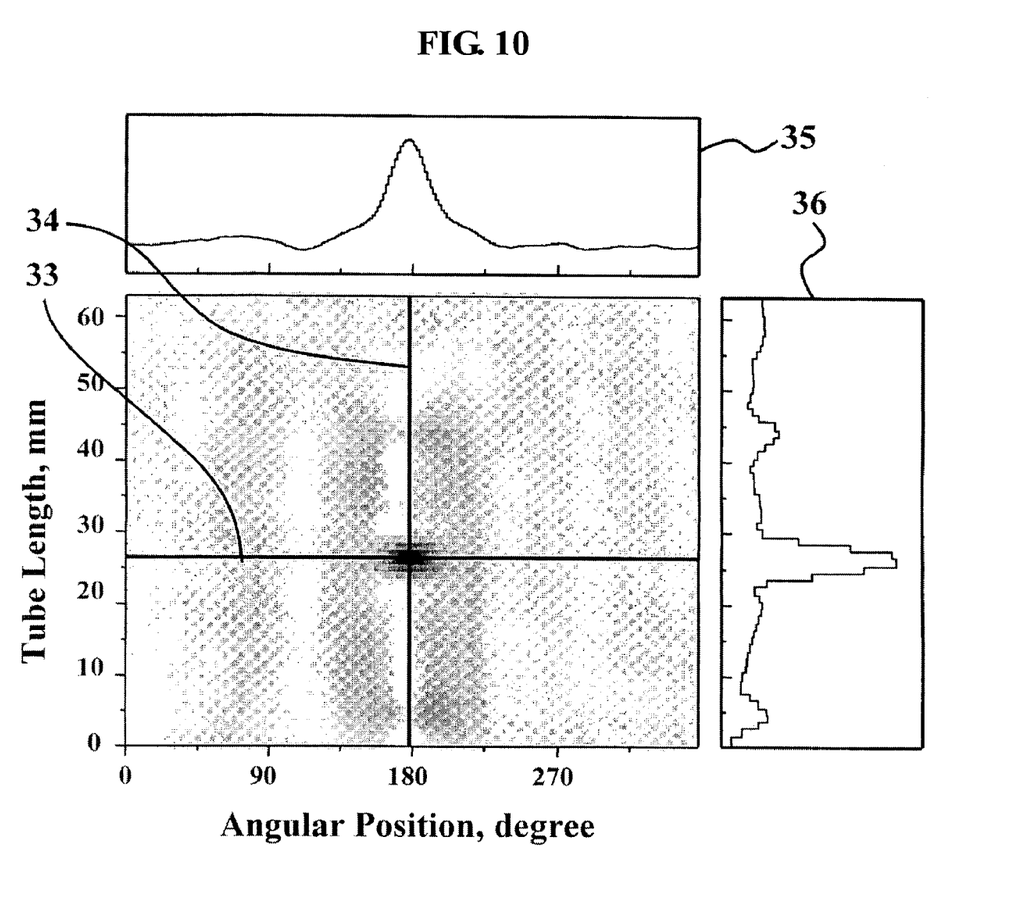
FIG. 10 is a distribution graph of the amplitude of an eddy current signal for each position in the direction of the circumference and length, measured by the coil for detecting a defect in the case a single crack in the direction of the length existing in a heat exchanger tube is detected by using a heat exchanger tube state detecting apparatus, according to the present invention.

FIG. 10 is a distribution graph of the amplitude of an eddy current signal for each position in the direction of the circumference and length, measured by the coil for detecting a defect in the case a single crack in the direction of the length existing in the second heat exchanger tube is detected by using a heat exchanger tube state detecting apparatus, according to the present invention.

Referring to FIG. 10, the change of signal amplitudes measured by the defect detecting eddy current coil is indicated by a difference in shading. The third horizon 33 is the position of 26.5 mm in the lengthwise direction and the third vertical 34 is the position of 178° in the circumferential direction, at which the signal amplitude is largest and thus the crack exists. The fifth graph 35 indicates a signal amplitude change for each circumferential location of a zone disposed on the third horizon 33, and the sixth graph 36 indicates a signal amplitude change for each lengthwise location of a zone disposed on the third vertical 34.

Figure 11:
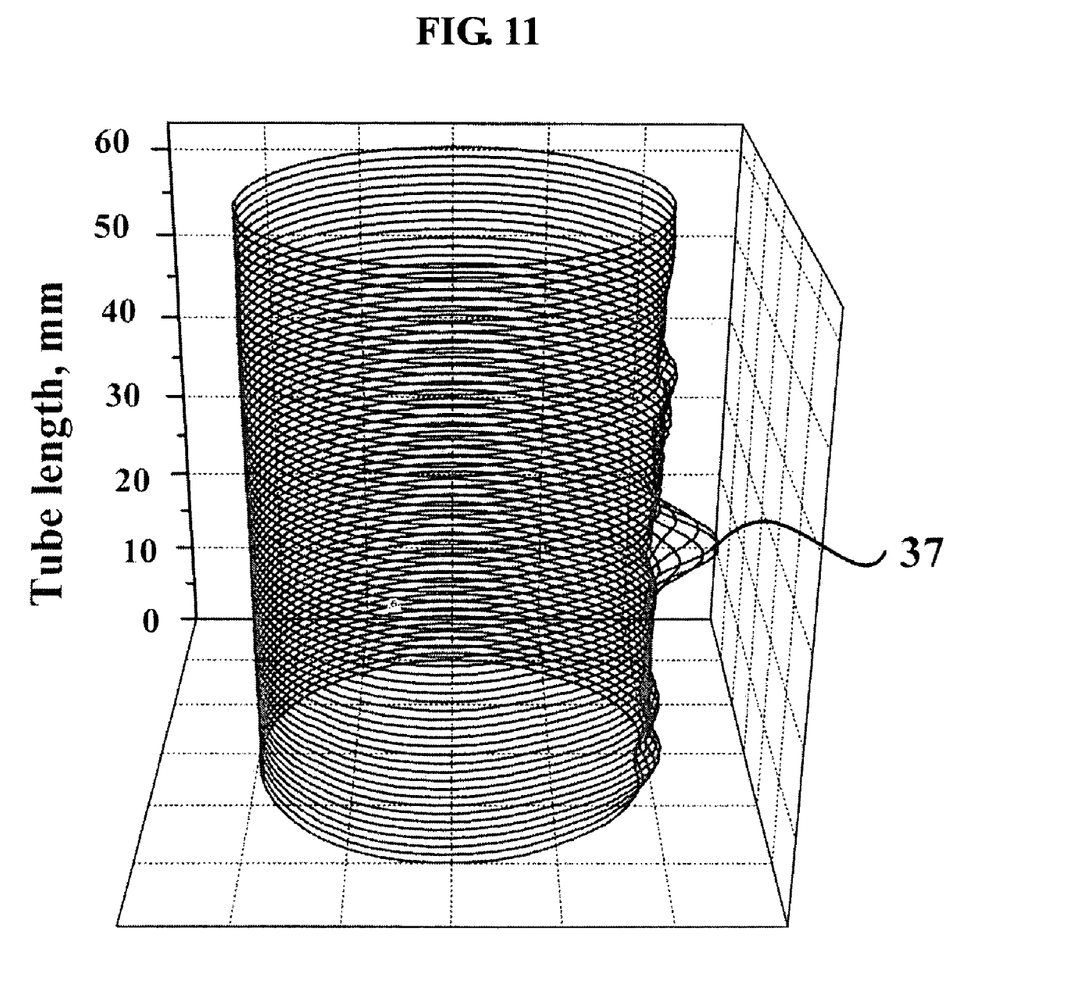
FIG. 11 is a three-dimensional graph of the amplitude distribution of the eddy current signal, measured by the coil for detecting a defect in the case a single crack in the direction of the length existing in a heat exchanger tube is detected by using a heat exchanger tube state detecting apparatus, according to the present invention.

FIG. 11 is a three-dimensional graph of amplitude distribution of the eddy current signal, measured by the coil for detecting a defect in the case a single crack in the direction of the length existing in the second heat exchanger tube sample is detected by using a heat exchanger tube state detecting apparatus, according to the present invention.

Referring to FIG. 11, the heat exchanger tube state detecting apparatus may recognize in three dimensions the number of defects of the heat exchanger tube to be one and the location 37 of the defect by using the three-dimensional graph of the amplitude distribution of the eddy current signal measured by the defect detecting eddy current coil.

Figure 12:
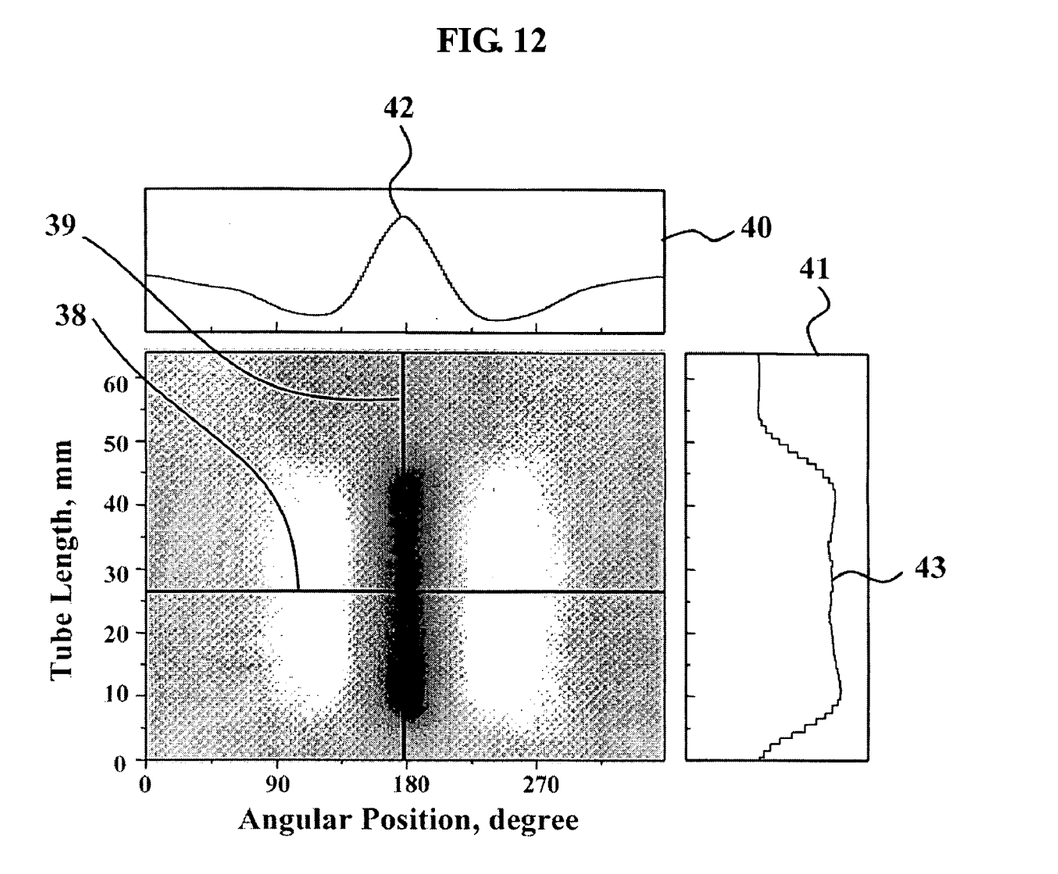
FIG. 12 is a distribution graph of the amplitude of an eddy current signal for each position in the direction of the circumference and length, measured by the coil for detecting a geometric transition in the case a bulge existing in a heat exchanger tube is detected by using a heat exchanger tube state detecting apparatus, according to the present invention.

FIG. 12 is a distribution graph of the amplitude of an eddy current signal for each position in the direction of the circumference and length, measured by the coil for detecting a geometric transition in the case a bulge existing in the second heat exchanger tube sample is detected by using a heat exchanger tube state detecting apparatus, according to the present invention.

Referring to FIG. 12, the heat exchanger tube state detecting apparatus synchronizes the data of eddy current signal amplitude measured from the geometric transition detecting eddy current coil with the data from the defect detecting eddy current coil. After synchronizing, the fourth horizon 38 and the fourth vertical 39 will have the same position as the third horizon 33 and the third vertical 34, thereby locating the position of the defect, respectively. The seventh graph 40 indicates a signal amplitude change for each circumferential location of a zone disposed on the fourth horizon 38, and the eighth graph 41 indicates a signal amplitude change for each lengthwise location of a zone disposed on the fourth vertical 39. The heat exchanger tube state detecting apparatus may recognize that the location of a defect is a position 42 that is a peak of a section in which a certain part is protruded on the circumferential location, from the seventh graph 40. Also, the heat exchanger tube state detecting apparatus may recognize that a section of approximately 40 mm in length (20 mm upward and 20 mm downward from the location of a crack) suffers protrusion 43 along the lengthwise direction, from the eighth graph 41.

Figure 13:
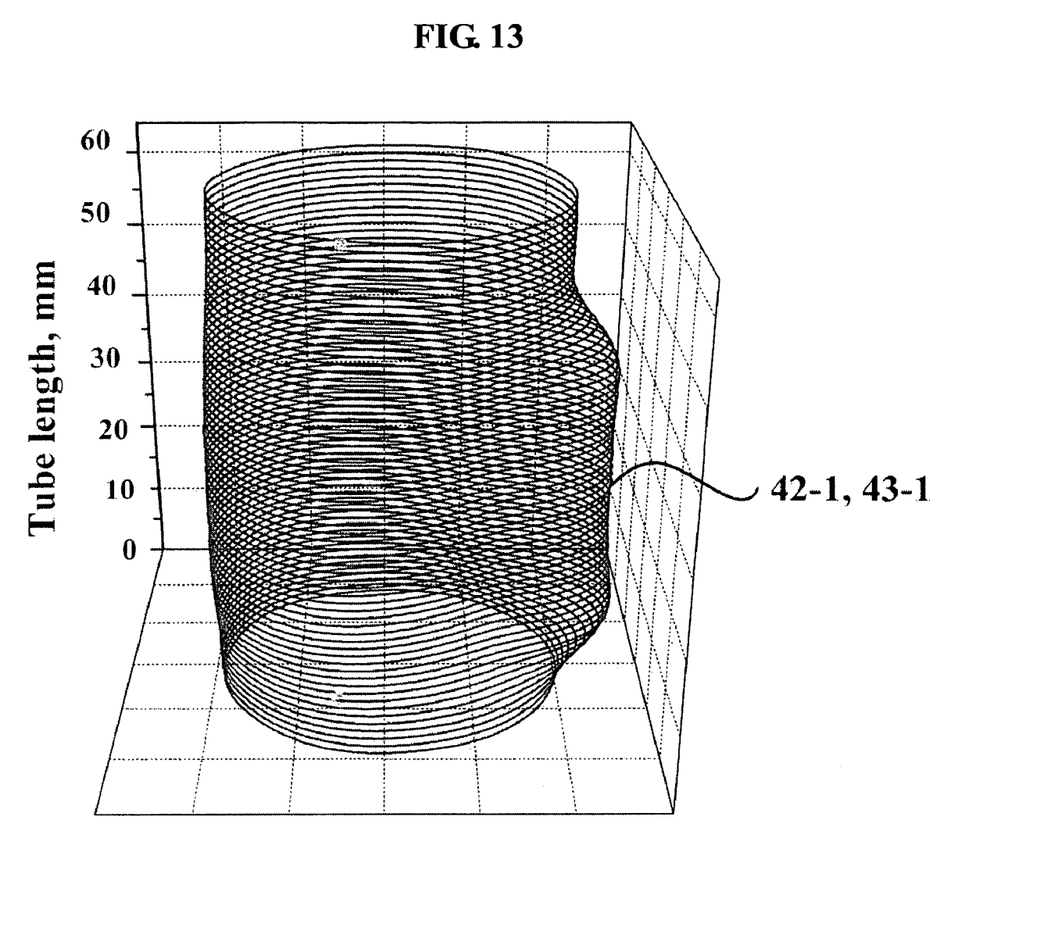
FIG. 13 is a three-dimensional graph of amplitude distribution of the eddy current signal, measured by the coil for detecting a geometric transition in the case a bulge existing in a heat exchanger tube is detected by using a heat exchanger tube state detecting apparatus, according to the present invention.

FIG. 13 is a three-dimensional graph of amplitude distribution of the eddy current signal, measured by the coil for detecting a geometric transition in the case a bulge existing in the second heat exchanger tube sample is detected by using a heat exchanger tube state detecting apparatus, according to the present invention.

Referring to FIG. 13, the heat exchanger tube state detecting apparatus may recognize in three dimensions the geometric transition 42-1 and 43-1 in which a part of the circumference is protruded over the length of approximately 40 mm from the distribution of the signal amplitude via the three-dimensional graph of the amplitude distribution of the eddy current signal measured by the geometric transition detecting eddy current coil.

Figure 14:
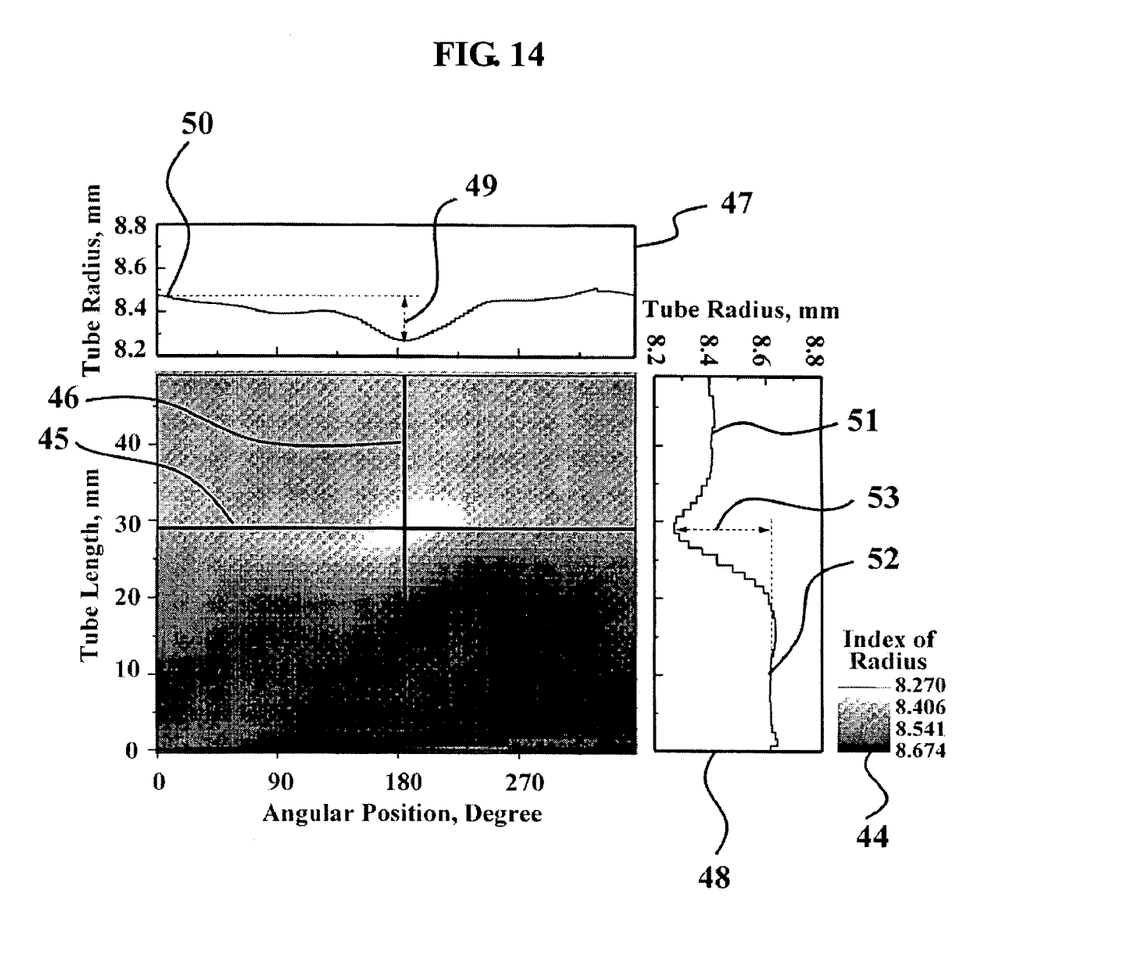
FIG. 14 is a distribution graph illustrating the measured radius for each position in the direction of the circumference and length, shown by quantifying the size of the geometric transition from the amplitude of an eddy current signal measured by the coil for detecting a geometric transition in the case a local dent existing in a heat exchanger tube is detected by using a heat exchanger tube state detecting apparatus, according to the present invention.

FIG. 14 is a distribution graph illustrating the measured radius for each position in the direction of the circumference and length, shown by quantifying the size of the geometric transition from the amplitude of an eddy current signal measured by the coil for detecting a geometric transition in the case a local dent existing in the first heat exchanger tube sample is detected by using a heat exchanger tube state detecting apparatus, according to the present invention.

Referring to FIG. 14, the heat exchanger tube state detecting apparatus obtains the correlation between the eddy current signal amplitude detected from the geometric transition detecting eddy current coil and the real size of the geometric transition by using a standard tube sample for calibration of the heat exchanger tube state detecting apparatus, in which various geometric transitions with already known size are embedded. The heat exchanger tube state detecting apparatus may detect and quantify the geometric transition in the heat exchanger tube by converting the amplitude of the eddy current signal caused by the geometric transition measured in an actual heat exchanger tube into the value of the real size from the correlation. As shown in FIG. 14, the heat exchanger tube state detecting apparatus may show a radius value measured for each position as a difference in shading by using the radius index. The fifth horizon 45 and the fifth vertical 46 locate a position in which the radius is smallest, namely, a position in which a dent is largest, as 29 mm in the lengthwise direction and 185° in the circumferential direction, respectively. The ninth graph 47 indicates a radius change for each circumference location of a zone disposed on the fifth horizon 45, and the tenth graph 48 indicates a radius change for each lengthwise location of a zone disposed on the fifth vertical 46. The ninth graph 47 also indicates the heat exchanger tube state detecting apparatus measures the maximum size of the dent 49 at 185° in the circumferential direction in terms of the radius change which is reduced by 0.20 mm with respect to position 50 at 5° corresponding to a 180° opposite circumferential position without dent. The heat exchanger tube state detecting apparatus may recognize the radius of the non-expanded region 51 of the heat exchanger tube is 8.40 mm, the radius of the expanded region 52 is 8.62 mm, and the increase of the radius caused by the expansion is approximately 0.22 mm, from the tenth graph 48. Also, the heat exchanger tube state detecting apparatus may obtain a quantified measurement result that the maximum size of dent 53 existing in the transition zone between the non-expanded region 51 and the expanded region 52 of the heat exchanger tube is approximately 0.35 mm in terms of the radius decrease with respect to the radius of expanded region 52, from the tenth graph 48.

Figure 15:
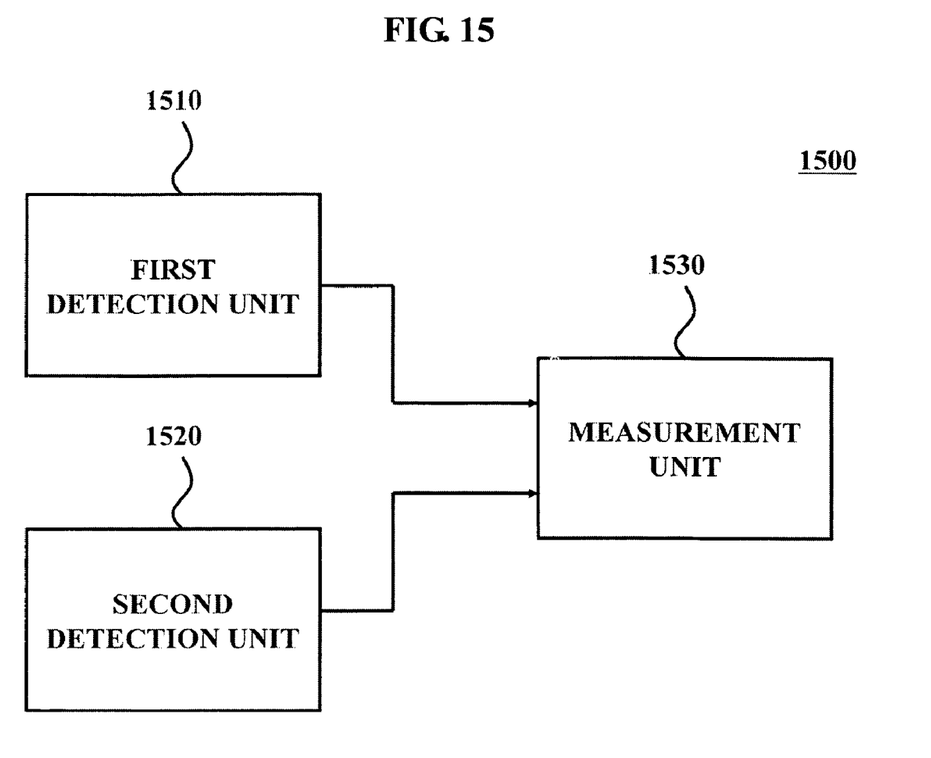
FIG. 15 is a configuration diagram of an apparatus for detecting the state of a heat exchanger tube, according to an embodiment of the present invention.

FIG. 15 is a configuration diagram of an apparatus for detecting the state of a heat exchanger tube, according to an embodiment of the present invention. The heat exchanger tube state detecting apparatus 1500 includes the first detection unit 1510, the second detection unit 1520, and the measurement unit 1530.

The first detection unit 1510 includes two or more different defect detecting eddy current coils separated at a certain circumferential distance on the same circumference of a cylindrical body and detects a defect occurring in the heat exchanger tube. The defect detecting eddy current coils may be wound to cross each other in a horizontal direction and a vertical direction and may be in contact with the inner surface of the heat exchanger tube via springs.

The first detection unit 1510 is rotated by a motor while moving up and down the heat exchanger tube in a straight line and may detect a defect existing on the inner/outer surfaces of the heat exchanger tube, such as a crack, a wear, a pit, and an intergranular corrosion.

The second detection unit 1520 includes two or more different geometric transition detecting eddy current coils separated at a certain circumferential distance on the same circumference of a cylindrical body and detects a geometric transition occurring in the heat exchanger tube. The geometric transition detecting eddy current coils may be wound to form a spiral and maintain a certain distance in order not to be in contact with the inner surface of the heat exchanger tube.

The second detection unit 1520 is rotated by a motor while moving up and down the heat exchanger tube in a straight line and may detect whether a geometric transition, such as an expansion, a dent, or a bulge, exist.

As shown in FIG. 1, the first detection unit 1510 and the second detection unit 1520 are disposed at the same circumferential location of the cylindrical probe bodies 3, 5, and 6, installed to have a certain distance in the lengthwise direction of the cylindrical probe bodies 3, 5, and 6, inserted into the heat exchanger tube, thereby detecting a defect and a geometric transition inside the heat exchanger tube.

The measurement unit 1530 collects data about the detected defect and the detected geometric transition signal and measures the location of the defect and the size of the geometric transition. The measurement unit identifies the type of the detected defect and the detected geometric transition and may make three-dimensional measurements of the location of the defect and the size of the geometric transition.

Figure 16:
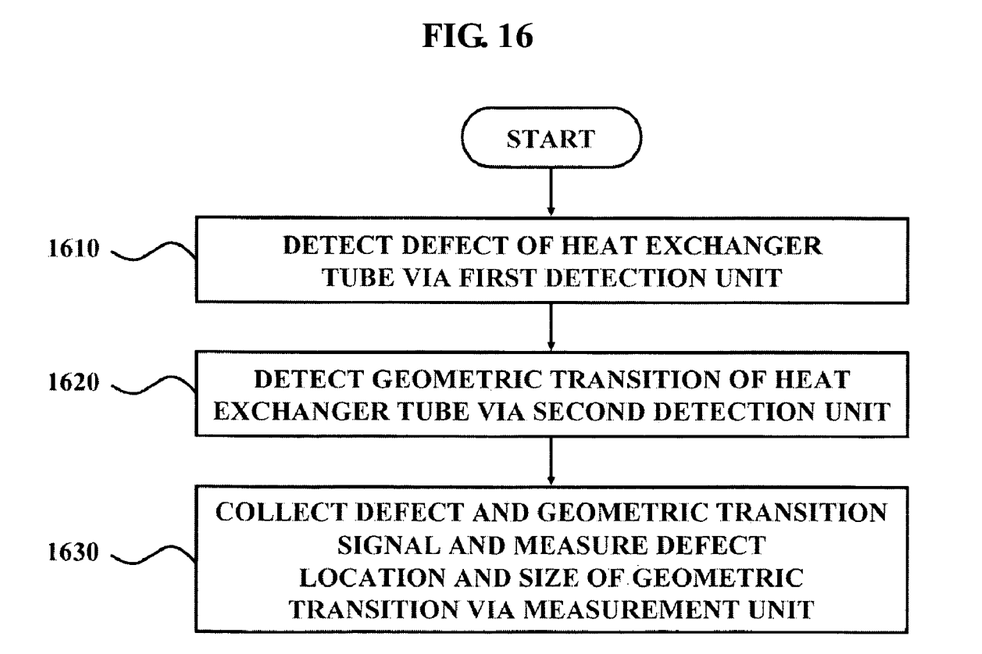
FIG. 16 is a flow chart illustrating a method of detecting the state of a heat exchanger tube, according to an embodiment of the present invention

FIG. 16 is a flow chart illustrating a method of detecting the state of a heat exchanger tube, according to an embodiment of the present invention.

In Step 1610, the heat exchanger tube state detecting apparatus detects a defect of a heat exchanger tube via the first detection unit. In this case, the first detection unit is inserted inside the heat exchanger tube, is rotated by a motor while moving up and down the heat exchanger tube in a straight line, and may detect a defect existing in the inner/outer surfaces of the heat exchanger tube, such as a crack, a wear, a pit, and an intergranular corrosion.

In Step 1620, the heat exchanger tube state detecting apparatus detects a geometric transition of a heat exchanger tube via the second detection unit. In this case, the second detection unit is inserted inside the heat exchanger tube, is rotated by a motor while moving up and down the heat exchanger tube, and may detect whether a geometric transition, such as an expansion, a dent, or a bulge, exists.

In Step 1630, the heat exchanger tube state detecting apparatus collects data about the detected defect and the detected geometric transition signal and may measure the location of the defect and the size of the geometric transition via a measurement unit.

According to the present invention, there is provided an apparatus for detecting a geometric transition in addition to a defect occurring in a heat exchanger tube and distinguishing the defect from the geometric transition.

Also, according to the present invention, a structural root cause of a defect occurring in a heat exchanger tube may be identified, and the information about the location of a geometric transition is provided to reduce the possibility of generating a human error in detecting a defect in the case a defect is caused by a geometric transition.

Also, according to the present invention, in comparison with a case of simply detecting a defect of a heat exchanger tube, the type of geometric transition, which can accelerate the initiation and the growth of a defect, is identified and the size of the geometric transition is measured, thereby improving the reliability in early detection of a defect.

Also, according to the present invention, the size of a geometric transition around a defect occurring in a heat exchanger tube is measured, and the residual stress applied on the defect and the growth rate of the defect are estimated to determine the risk of the defect that may occur in a heat exchanger tube.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for detecting the state of a heat exchanger tube, comprising:
   a first detection unit detecting a defect of the heat exchanger tube; and
   a second detection unit detecting a geometric transition of the heat exchanger tube,
   wherein the first detection unit and the second detection unit are disposed at the same circumferential position of a cylindrical body respectively, installed to have a certain distance in the lengthwise direction of the cylindrical body, and inserted inside the heat exchanger tube.

2. The apparatus of claim 1, further comprising a measurement unit which collects data about the signals from the detected defect and the detected geometric transition and measures the position in which the defect detection occurs and the geometric transition exists, as well as the size of the geometric transition.

3. The apparatus of claim 1, wherein the first detection unit moves up and down the heat exchanger tube in a straight line while being rotated by a motor and detects a crack, a wear, a pit, or a grain boundary corrosion which exist on the outer or inner surface of the heat exchanger tube.

4. The apparatus of claim 1, wherein the second detection unit moves up and down the heat exchanger tube in a straight line while being rotated by a motor and detects whether a geometric transition, such as an expansion, a dent, or a bulge, exists.

5. The apparatus of claim 1, wherein the first detection unit includes two or more different eddy current coils which are separated from each other at a certain circumferential distance on the same circumference of the cylindrical body, in which one of the eddy current coils is wound in a horizontal direction and a vertical direction to cross each other.

6. The apparatus of claim 1, wherein the second detection unit includes two or more different eddy current coils which are separated from each other at a certain circumferential distance on the same circumference of the cylindrical body, in which one of the eddy current coils is wound to form a spiral.

7. The apparatus of claim 1, wherein the first detection unit includes an eddy current coil for detecting a defect of the heat exchanger tube, which is in contact with the inner surface of the heat exchanger tube via springs.

8. The apparatus of claim 1, wherein the second detection unit includes an eddy current coil for detecting a geometric transition of the heat exchanger tube, which keeps a certain distance from the inner surface of the heat exchanger tube in order not to be in contact with the inner surface of the heat exchanger tube.

9. The apparatus of claim 1, further comprising support legs elastically contacting with the inner surface of the heat exchanger tube in the front-end and rear-end of the cylindrical body, which support the cylindrical body to be located in the center of the heat exchanger tube.

10. The apparatus of claim 1, wherein:
the first detection unit includes the first eddy current coil for detecting a defect of the heat exchanger tube; and
the second detection unit includes the second eddy current coil for detecting a geometric transition of the heat exchanger tube, in which the first eddy current coil and the second eddy current coil are installed in the cylindrical body, separately, to have a certain distance in the lengthwise direction,
further comprising support legs elastically contacting with the inner surface of the heat exchanger tube in both ends of the cylindrical body and in the central portion of the cylindrical body between the first eddy current coil and the second eddy current coil.

11. The apparatus of claim 2, wherein the measurement unit identifies the type of the detected defect and the detected geometric transition and makes three dimensional measurements of the position where the defect occurs and the geometric transition exists, as well as the size of the geometric transition.

12. A method of detecting the state of a heat exchanger tube, comprising:
a step of detecting a defect of the heat exchanger tube, the step performed by a first detection unit;
a step of detecting a geometric transition of the heat exchanger tube, the step performed by a second detection unit; and
a step of collecting data about the signals from the detected defect and the detected geometric transition, and measuring the position in which the defect occurs and the geometric transition exists, as well as the size of the geometric transition, the step performed by a measurement unit,
wherein the first detection unit and the second detection unit are disposed, separately, at the same circumferential position of a cylindrical body, installed to have a certain distance in the lengthwise direction of the cylindrical body, and inserted inside of the heat exchanger tube.

* * * * *